US006140482A

United States Patent [19]
Iyer et al.

[11] Patent Number: 6,140,482
[45] Date of Patent: *Oct. 31, 2000

[54] PRIMARY PHOSPHORAMIDATE INTERNUCLEOSIDE LINKAGES AND OLIGONUCLEOTIDES CONTAINING THE SAME

[75] Inventors: Radhakrishnan P. Iyer, Shrewsbury; Theresa Devlin, Jamaica Plain; Ivan Habus, Shrewsbury; Dong Yu, Shrewsbury; Sudhir Agrawal, Shrewsbury, all of Mass.

[73] Assignee: Hybridon, Inc., Milford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/519,318

[22] Filed: Aug. 25, 1995

Related U.S. Application Data

[63] Continuation-in-part of application No. 08/457,198, Jun. 1, 1995, abandoned.

[51] Int. Cl.$^7$ .................................................. C07H 21/00
[52] U.S. Cl. ............................ 536/22.1; 435/6; 436/501; 514/44; 536/24.5
[58] Field of Search .................. 435/6, 691, 810; 436/501; 514/44; 536/23.1, 24.1, 24.3–24.33, 22.1, 24.5; 935/77, 78

[56] References Cited

U.S. PATENT DOCUMENTS

| | | | |
|---|---|---|---|
| 5,149,798 | 9/1992 | Agrawal et al. | 536/27 |
| 5,212,295 | 5/1993 | Cook | 536/26.7 |
| 5,264,566 | 11/1993 | Froehler et al. | 536/25.34 |
| 5,476,925 | 12/1995 | Letsinger et al. | 536/23.1 |

FOREIGN PATENT DOCUMENTS

WO 93/08296  4/1993  WIPO .

OTHER PUBLICATIONS

S. Agrawal, Ed., "Methods in Molecular Biology, vol. 20: Protocols for Oligonucleotides and Analogs", pp. 165–189, Humana Press, 1993.
F. Eckstein, Ed., "Oligonucleotides and Analogues: A Practical Approach", pp. 87–108 (1991).
Uhlmann and Peyman, Chem. Rev. 90:543 (1990).
Agrawal and Iyer, "Curr. Op. in Biotech. 6", 12–19 (1995).
Khorana et al., "J. Molec. Biol. 72", 209–217 (1972).
Beaucage and Carruthers, "Tetrahedron Lett. 22", 1859–1862 (1981).
Agrawal and Goodchild, "Tetrahedron Lett. 28", 3539–3542 (1987).
Connolly et al., "Biochemistry 23", 3443–3453 (1984).
Jager et al., "Biochemistry 27", 7237–7246 (1988).
Agrawal et al, "Proc. Natl. Acad. Sci. USA 85", 7079–7083 (1988).
Galbraith et al., "Antisense Research and Development 4", 201–206 (1994).
Agrawal and Tang, "Antisense Research and Development 2", 261–266 (1992).
Iyer et al., "Tetrahedron Asymmetry 6", 1051–1054 (1995).
Debenham et al. (1995) *Journal of the American Chemical Society* 117:3302–3303.
Kraszewski et al. (1993) *Journal of the Chemical Society, Perkin Transactions 1*, pp. 1699–1704.
Jones et al. (1985) *Journal of the Chemical Society, Perkin Transactions 1*, pp. 199–202.
Iyer et al. (1995) *Tetrahedron: Asymmetry* 6:1051–1054.
Iyer et al. (1995) *Journal of Organic Chemistry* 60:5388–5389.

*Primary Examiner*—Ardin H. Marschel
*Attorney, Agent, or Firm*—Hale and Dorr LLP; Wayne A. Keown

[57] ABSTRACT

The invention provides new primary phosphoramidate internucleoside linkages that are less sterically constrained than existing phosphoramidate linkages, as well as oligonucleotides containing such linkages and processes for making and methods for using such oligonucleotides.

6 Claims, No Drawings

PRIMARY PHOSPHORAMIDATE INTERNUCLEOSIDE LINKAGES AND OLIGONUCLEOTIDES CONTAINING THE SAME

This is a continuation-in-part of U.S. Ser. No. 08/457,198, filed Jun. 1, 1995, now abandoned.

BACKGROUND OF THE INVENTION

1. Field of the Invention

The invention relates to synthetic oligonucleotides and to their use in molecular biology applications and in the antisense therapeutic approach.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology, Vol 20: Protocols for Oligonucleotides and Analogs* pp. 165–189 (S. Agrawal, Ed., Humana Press, 1993/); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6, 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron Lett.* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Carruthers, *Tetrahedron Lett.* 22, 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), teaches synthesis of oligonucleotide methylphosphonates using phosphoramidite chemistry. Connolly et al., *Biochemistry* 23, 3443 (1984), discloses synthesis of oligonucleotide phosphorothioates using phosphoramidite chemistry. Jager el al., *Biochemistry* 27, 7237 (1988), discloses synthesis of oligonucleotide phosphoramidates using phosphoramidite chemistry. Agrawal et al., *Proc. Natl. Acad. Sci. USA* 85, 7079–7083 (1988), discloses synthesis of oligonucleotide phosphoramidates and phosphorothioates using H-phosphonate chemistry.

The routine synthesis of oligonucleotides is presently carried out using various N-acyl protecting groups for the nucleoside bases, such as isobutyryl (for guanine), and benzoyl for adenine and cytosine. After the synthesis of the oligonucleotides is carried out using either phosphoramidite chemistry or H-phosphonate chemistry, the protecting groups are removed by treatment with ammonia at 55–60° C. for 5–10 hours. Using these protecting groups, PO oligonucleotides and other modified oligonucleotides can be synthesized. But in certain instances where modified oligonucleotides are functionalized with base-sensitive groups, the functionalities often get removed while the deprotection is being carried out.

This limitation in the oligonucleotide synthesis procedure has resulted in the inability to synthesize certain modified oligonucleotides that may have considerable utility. For example, current synthesis procedures allow the synthesis of some, but not all possible oligonucleotide phosphoramidates, because some of these compounds are labile under the highly alkaline conditions required for deprotection of the nucleoside base. Oligonucleotides containing primary phosphoramidate internucleoside linkages, for example, have not previously been possible to synthesize for this reason. In the case of the oligonucleotide phosphoramidates, this inability to synthesize oligonucleotides containing primary phosphoramidate internucleoside linkages has probably slowed their development as optimally useful compounds for molecular biology applications and the antisense therapeutic approach. This is likely because the oligonucleotide phosphoramidates that have been developed all have relatively large chemical constituents in place of one of the nonbridging oxygen atoms on the phosphate backbone, which may lead to steric hindrance of the ability of the oligonucleotide to bind to its target. It would be valuable to have better phosphoramidate linkages, since such linkages can be made uncharged, which could result in a reduction in oligonucleotide side effects that are attributable to the polyanionic character of the oligonucleotides. For example, Galbraith et al., Antisense Research and Development 4: 201–206 (1994) disclose complement activation by oligonucleotides. Henry et al., Pharm. Res. 11: PPDM8082 (1994) discloses that oligonucleotides may potentially interfere with blood clotting.

There is therefore, a need for new phosphoramidate linkages that are less sterically constrained than existing phosphoramidate linkages, and for oligonucleotides containing such linkages. Ideally, such oligonucleotides should be easy to synthesize and should be capable of containing numerous other beneficial modifications.

BRIEF SUMMARY OF THE INVENTION

The invention provides new phosphoramidate linkages that are less sterically constrained than existing phosphoramidate linkages, as well as oligonucleotides containing such linkages and processes for making and methods for using such oligonucleotides. The oligonucleotides according to the invention are easy to synthesize and can conveniently be made to contain numerous other beneficial modifications.

In a first aspect, the invention provides a primary phosphoramidate internucleoside linkage having the structure I:

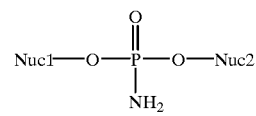

wherein "Nuc1" represents the 3' position of a first nucleoside and "Nuc2" represents the 5' position of a second nucleoside. This structure is the smallest possible phosphoramidate internucleoside linkage, and as such, should contribute less to any steric constraints to the oligonucleotide than other phosphoramidate linkages. The linkage provides the benefit of having a molecular size that is similar to that of a natural phosphodiester linkage, but at the same time having nonionic character. Such an internucleoside linkage should confer upon an oligonucleotide a reduction in polyanion-mediated side effects and should also improve cellular uptake of the oligonucleotide.

In a second aspect, the invention provides a simple process for synthesizing an oligonucleotide containing from one to about all primary phosphoramidate internucleoside linkages. This process comprises condensing a nucleoside H-phosphonate with another nucleoside, wherein at least one of the nucleosides has a nucleoside base-protective group, to produce adjacent nucleosides coupled by an H-phosphonate internucleoside linkage, wherein at least one of the nucleosides has a nucleoside base-protective group, aminating the H-phosphonate internucleoside linkage to produce a primary phosphoramidate linkage, and chemoselectively removing the nucleoside base-protective group without cleaving the primary phosphoramidate linkage. This process allows for synthesis, for the first time, of oligonucleotides containing primary phosphoramidate internucleoside linkages, because the process utilizes a new nucleoside base protective group that can be chemoselectively removed, in contrast to the harsh deprotective conditions utilized by known methods, which would cleave the sensitive primary phosphoramidate linkage. Importantly, the process according to the invention is compatible with and can be used in conjunction with any of the well known oligonucleotide synthetic chemistries, including the H-phosphonate, phosphoramidate and phosphotriester chemistries. Consequently, the process according to the invention can be used to synthesize oligonucleotides having primary phosphoramidate linkages at some internucleoside positions and other linkages at other internucleoside positions.

Thus, in a third aspect, the invention provides oligonucleotides containing from one to about all primary phosphoramidate internucleoside linkages. In embodiments of oligonucleotides according to this aspect of the invention that have fewer than all primary amidate internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible. Oligonucleotides containing such a mixture of internucleoside linkages are referred to herein as mixed backbone oligonucleotides. In some preferred embodiments of mixed backbone oligonucleotides according to the invention, the internucleoside linkages that are not primary phosphoramidate linkages are selected from the group consisting of phosphodiester and phosphorothioate internucleoside linkages. In some preferred embodiments of mixed backbone oligonucleotides according to the invention, several adjacent nucleosides comprising one region of the oligonucleotide are connected by primary phosphoramidate linkages, and several other adjacent nucleosides comprising another region of the oligonucleotide are connected by a different type of internucleoside linkage. These preferred oligonucleotides are referred to herein as "chimeric" oligonucleotides. Oligonucleotides according to the invention are useful for a variety of purposes. For example, they can be labelled with a reporter group and used as probes in conventional nucleic acid hybridization assays. They can also be used as antisense "probes" of specific gene function by being used to block the expression of a specific gene in an experimental cell culture or animal system and to evaluate the effect of blocking such specific gene expression. In this use, oligonucleotides according to the invention are preferable to traditional "gene knockout" approaches because they are easier to use and can be used to block specific gene expression at selected stages of development or differentiation. Finally, oligonucleotides according to the invention are useful in the antisense therapeutic approach. In this use, oligonucleotides according to the invention should have reduced polyanion-mediated side effects and improved cellular uptake.

DETAILED DESCRIPTION OF THE PREFERRED EMBODIMENTS

The invention relates to synthetic oligonucleotides and to their use in molecular biology applications and in the antisense therapeutic approach. The patents and publications identified in this specification are within the knowledge of those skilled in this field and are hereby incorporated by reference in their entirety.

The invention provides new phosphoramidate linkages that are less sterically constrained than existing phosphoramidate linkages, as well as oligonucleotides containing such linkages and processes for making and methods for using such oligonucleotides. The oligonucleotides according to the invention are easy to synthesize and can conveniently be made to contain numerous other beneficial modifications.

In a first aspect, the invention provides a primary phosphoramidate internucleoside linkage having the structure I:

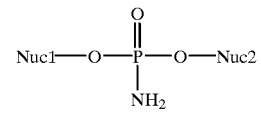

wherein "Nuc1" represents the 3' position of a first nucleoside and "Nuc2" represents the 5' position of a second nucleoside. This structure is the smallest possible phosphoramidate internucleoside linkage, and as such, should contribute less to any steric constraints to the oligonucleotide than other phosphoramidate linkages. Accordingly, this internucleoside linkage should have less effect on the ability of an oligonucleotide to hybridize with a complementary nucleic acid. The linkage provides the benefit of having a molecular size that is similar to that of a natural phosphodiester linkage, but at the same time having nonionic character. Such an internucleoside linkage should confer upon an oligonucleotide a reduction in polyanion-mediated side effects and should also improve cellular uptake of the oligonucleotide.

For purposes of the invention, the term "oligonucleotide" includes polymers of two or more deoxyribonucleotide or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

In a second aspect, the invention provides a simple process for synthesizing an oligonucleotide containing from one to about all primary phosphoramidate internucleoside linkages. This process comprises coupling a nucleoside H-phosphonate with another nucleoside, wherein at least one of the nucleosides has a nucleoside base-protective group, to produce adjacent nucleosides coupled by an H-phosphonate internucleoside linkage, wherein at least one of the nucleosides has a nucleoside base-protective group, aminating the H-phosphonate internucleoside linkage to produce a primary phosphoramidate linkage, and chemoselectively removing the nucleoside base-protective group without cleaving the primary phosphoramidate linkage. To remove the oligonucleotide from the support without damaging the primary phosphoramidate internucleoside linkage, the support-bound oligonucleotide can then be treated with ammonia in dioxane.

This process allows for synthesis, for the first time, of oligonucleotides containing primary phosphoramidate internucleoside linkages, because the process utilizes a new nucleoside base protective group that can be chemoselectively removed, in contrast to the harsh deprotective conditions utilized by known processes, which would cleave the sensitive primary phosphoramidate linkage. The new nucleoside base protective group has the general structure II:

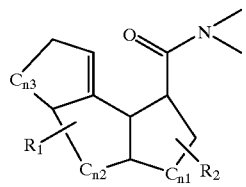

where $n_1$, $n_2$, and $n_3$ are independently 0–10, the ring structures shown may be aromatic or heterocyclic, the nitrogen displayed is the protected amino moiety of the nucleoside base, and $R_1$ and $R_2$ are independently hydrogen, or an alkyl, aryl, aralkyl, ether, hydroxy, nitrile, nitro, ester, carboxyl, or aldehyde group.

In a preferred embodiment, compound II has $n_1$, $n_2$ and $n_3$ values of 0 and thus takes the form N-pent-4-enoyl, i.e., $CH_2=CH(CH_2)_2CO-$ (III). Compounds II and III protect the nucleoside base amino moieties by forming amide linkages, as in: where the nitrogen displayed is the protected amino moiety of the nucleoside base B. The chemoselective removal of the nucleoside base protective group is accomplished by using a chemoselective removing agent. In certain preferred embodiments, the chemoselective removing agent is selected from the group consisting of halogens, especially $Br_2$, $Cl_2$ and $I_2$, any of which are preferably in water, or in pyridine/ROH, wherein R is an alkyl, aralkyl or aryl group having 1–10 carbon atoms, or as an N-halosuccinimide.

Importantly, the process according to the invention is compatible with and can be used in conjunction with any of the well known oligonucleotide synthetic chemistries, including the H-phosphonate, phosphoramidate and phosphotriester chemistries. Consequently, the process according to the invention can be used to synthesize oligonucleotides having primary phosphoramidate linkages at some internucleoside positions and other linkages at other internucleoside positions. In one preferred embodiment, synthesis is carried out on a suitable solid support using either H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)). Synthesis on such a solid support begins with coupling a nucleoside synthon according to the invention to a nucleoside that is covalently linked to the solid support (i.e., linked to a functionality on the solid support, preferably an amino or hydroxyl functionality). More generally, the process according to the invention can be used with any of the chemistries commonly used for oligonucleotide synthesis, whether in solution phase or in solid phase.

The versatility of chemical synthetic approach of the process according to the invention makes the process according to the invention suitable for the synthesis of any of a broad class of compounds, all of which are referred to herein as "oligonucleotides", as previously defined herein.

In a third aspect, the invention provides oligonucleotides containing from one to about all primary phosphoramidate internucleoside linkages. Preferably, such oligonucleotides will have from about 12 to about 50 nucleotides, most preferably from about 17 to about 35 nucleotides. Preferably, such oligonucleotides will have a nucleotide sequence that is complementary to a genomic region, a gene, or an RNA transcript thereof. The term complementary means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition. The gene sequence or RNA transcript sequence to which the modified oligonucleotide sequence is complementary will depend upon the biological effect that is sought to be modified. In some cases, the genomic region, gene, or RNA transcript thereof may be from a virus. Preferred viruses include, without limitation, human immunodeficiency virus (type 1 or 2), influenza virus, herpes simplex virus (type 1 or 2), Epstein-Barr virus, cytomegalovirus, respiratory syncytial virus, influenza virus, hepatitis B virus, hepatitis C virus and papilloma virus. In other cases, the genomic region, gene, or RNA transcript thereof may be from endogenous mammalian (including human) chromosomal DNA. Preferred examples of such genomic regions, genes or RNA transcripts thereof include, without limitation, sequences encoding vascular endothelial growth factor (VEGF), beta amyloid, DNA methyltransferase, protein kinase A, ApoE4 protein, p-glycoprotein, c-MYC protein, BCL-2 protein, protein kinase A and CAPL. In yet other cases, the genomic region, gene, or RNA transcript thereof may be from a eukaryotic or prokaryotic pathogen including, without limitation, *Plasmodium falciparum*, *Plasmodium malarie*, *Plasmodium ovale*, Schistosoma spp., and *Mycobacterium tuberculosis*.

In embodiments of oligonucleotides according to this aspect of the invention that have fewer than all primary amidate internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible. In certain preferred embodiments, the other internucleoside linkages are phosphodiester or phosphorothioate linkages. In the case of phosphorothioate internucleoside linkages, the linkages may be phosphorothioate mixed enantiomers or stereoregular phosphorothioates (see Iyer et al., Tetrahedron Asymmetry 6: 1051–1054 (1995).

Oligonucleotides containing such a mixture of internucleoside linkages are referred to herein as mixed backbone oligonucleotides. In some preferred embodiments of mixed backbone oligonucleotides according to the invention, several adjacent nucleosides comprising a first region of the oligonucleotide are connected by primary phosphoramidate linkages, and several other adjacent nucleosides comprising a second region of the oligonucleotide are connected by a different type of internucleoside linkage. These preferred oligonucleotides are referred to herein as "chimeric" oligonucleotides. In certain particularly preferred chimeric oligonucleotides according to the invention, the oligonucleotide comprises a primary phosphoramidate region and a phorothioate and/or phosphodiester region. In this context, a "primary phosphoramidate region" is a region within an oligonucleotide of from about 2 to about 15 contiguous nucleosides linked to each other through primary phosphoramidate linkages according to the invention, I. A "phosphorothioate region" is a region within an oligonucleotide of from about 4 to about 20 contiguous nucleosides linked to each other through phosphorothioate linkages. A "phosphodiester region" is a region within an oligonucleotide of from about 4 to about 20 contiguous nucleosides linked to each other through phosphodiester linkages. In most preferred chimeric oligonucleotides according to the invention, the oligonucleotide comprises a phosphorothioate or phosphodiester region flanked on either side by a primary phosphoramidate region, or alternatively, a primary phosphoramidate region flanked on either side by a phosphorothioate or phosphodiester region. In one preferred embodiment the nucleosides of the primary phosphoramidate region are 2'-O-substituted ribonucleotides, as defined above herein. Preferred chimeric oligonucleotides according to the invention are further characterized by having the ability to acivate RNaseH.

Oligonucleotides according to the invention are useful for a variety of purposes. For example, they can be labelled with a reporter group and used as probes in conventional nucleic acid hybridization assays. They can also be used as antisense "probes" of specific gene function by being used to block the expression of a specific gene in an experimental cell culture or animal system and to evaluate the effect of blocking such specific gene expression. This is accomplished by administering to a cell or an animal an oligonucleotide according to the invention that has a nucleotide sequence that is complementary to a specific gene that is expressed in the cell or animal to inhibit the expression of the specific gene, and observing the effect of inhibiting the expression of the specific gene. In this use, oligonucleotides according to the invention are preferable to traditional "gene knockout" approaches because they are easier to use and can be used to block gene specific gene expression at selected stages of development or differentiation.

Finally, oligonucleotides according to the invention are useful in the antisense therapeutic approach. In this use, oligonucleotides according to the invention should have reduced polyanion-mediated side effects and improved cellular uptake. For therapeutic use, oligonucleotides according to the invention may optionally be formulated with any of the well known pharmaceutically acceptable carriers or diluents. This formulation may further contain one or more additional oligonucleotides according to the invention. Alternatively, this formulation may contain one or more other antisense oligonucleotide, such as an oligonucleotide phosphorthioate, a RNA/DNA hybrid oligonucleotide, or a chimeric oligonucleotide containing known internucleoside linkages, or it may contain any other pharmacologically active agent.

Therapeutic use of oligonucleotides according to the invention is for treating a disease caused by aberrant gene expression. This is accomplished by administering to an individual having the disease a therapeutically effective amount of an oligonucleotide according to the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression. Preferably, such administation should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may desirable to administer simultaneously, or sequentially a therapeutically effective amount of one or more of the therapeutic compositions of the invention to an individual as a single treatment episode.

The following examples are intended to further illustrate certain preferred embodiments of the invention and are not limiting in nature.

EXAMPLE 1

Preparation of N-pent-4-enoyl 2'-deoxy Adenosine (dA Npr)

2'-Deoxyadenosine (Mallinkckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4 g, 20 mmol) was added and the contents stirred. After 15 min triethyl amine (3 ml) was added and the contents stirred for 2–3 h. The reaction slurry was cooled to 0–5° C. and 10 ml of water was added. After 5 min., 28% $NH_4OH$ (10 ml) was added. The resulting clear solution was evaporated to dryness. Water (150 ml) was added and the reaction mixture was extracted with ethylacetate:ether (50 ml, 1:1). The aqueous layer was separated and concentrated to a small volume. Upon leaving at room temperature, a white precipitate of the title compound was obtained. Filtration and drying gave ca. 3.5 g of pure title compound. Several experiments repeating the above procedure, using larger scale of operation, gave the title compound in 85–90% yield.

The same general procedure can be employed for the preparation of dG and dC protected nucleosides.

EXAMPLE 2

Preparation of 5'-O-DMT-N-4-pent-4-enoyl-nucleoside Synthons

The title compound was prepared by adopting a procedure as described by Froehler in Protocols for Oligonucleotides and analogs, Agrawal, S. Ed., pp. 63–80 as given below:

To 544 mg (1.63 mmol) of dA(N-pr) in 20 ml of anhydrous pyridine was added 1.108 g (3.3 mmol) of dimethoxytritylchloride. The reaction mixture was stirred at room temperature for 12 h. The reaction mixture was evaporated to dryness. The residue was chromatographed over silica gel 60 and eluted with $CH_2Cl2:CH_3OH:(Et)3N$ to give 0.73 of 5'-O-DMT-N-4-pent-4-enoyl-2'-deoxyadenosine as a white foamy material.

To a stirred solution of 1,2,4 triazole (0.944 g, 13.3 mmol) and triethylamine (5.5 ml, 30 mmol) in anhydrous $CH_2Cl_2$ (40 ml) was added $PCl_3$ (0.35 ml, 3.9 mmol) at room temperature under argon. After 30 min, the reaction mixture was cooled to 0° C. and 5'-DMT-protected nucleoside (500 mg, 0.88 mmol) in 15 ml $CH_2Cl_2$ was added dropwise over 10–15 min at 0° C. and allowed to warm to room temperature. The reaction mixture was poured into 1M triethylammoniumbicarbonate (TEAB) (75 ml, pH 8.5) with stirring. The mixture was transferred to a separatory funnel and the phases separated. The aqueous phase was extracted with methylene chloride and the combined organic phase washed with 1M TEAB (1×50 ml). The organic layer was dried over sodium sulfate and evaporated to dryness. The solid product thus obtained was purified by chromatography over silica gel. Elution with $CH_2Cl_2:CH_3OH:(Et)_3N$ (18:1:1) gave 0.065 g of the title compound.

Other H-phosphonate nucleosides are similarly prepared in overall yields ranging from 70–90%.

Similarly nucleoside 5'-O-DMT-3'-6-cyanoethyl-N,N-diisopropylphosphoramidites and 5'+O-DMT-3'-N-N-diisopropylphosphoramidites were prepared using standard protocols as described by Beaucage, S. L., in Protocols for Oligonucleotides and Analogs, Agrawal, S., Ed., pp. 33–61.

EXAMPLE 3

Solid Phase coupling of Nucleoside Synthons, Introduction of the Primary Phosphoramidate Linkage and Removal of Base Protective Groups Nucleoside synthons prepared according to Example 2 were coupled using solid phase H-phosphonate methodology (Froehler ref. above). The support bound oligonucleotide H-phosphonate was then treated with a solution of $NH_3$ (0.5 M in dioxane/$CCl_4$, 1:1) at ambient temperature for 30 minutes to give the corresponding support-bound primary phosphoramidate dinucleotide. Exposure to a solution of 2% $I_2$ in pyridine:methanol (98:2) for 30 minutes, followed by treatment with a saturated solution of $NH_3$ in dioxane at 55° C. for 12–16 hours furnished the free primary phosphoramidate dinucleotide in greater than 97%.

EXAMPLE 4

Relative Nuclease Resistance of Oligonucleotides Containing Primary Phosphoramidate Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 3, or by incorporating the protocol of Example 3 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266 (1992)). To test the relative nuclease resistance of these oligonucleotides the oligonucleotides are treated with snake venom phosphodiesterase (SVPD). About 0.2 $A_{260}$ units of oligonucleotide is dissolved in 500 microliters buffer (40 mM $NH_4CO_3$, pH 7.0, 20 mM $MgCl_2$) and mixed with 0.1 units SVPD. The mixture is incubated at 37° C. for 420 minutes. After 0, 200 and 420 minutes, 165 microliter aliquots are removed and analyzed using ion exchange HPLC. Oligonucleotides containing primary phosphoramidate internucleoside linkages are expected to have greater nuclease resistance than oligonucleotides containing exclusively phosphodiester or phosphorothioate internucleoside linkages.

EXAMPLE 5

Duplex Stability of Oligonucleotides Containing Primary Phosphoramidate Internucleoside Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 3, or by incorporating the protocol of Example 3 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266 (1992)). The oligonucleotides are tested for their ability to form duplexes with complementary oligodeoxyribonucleotides and oligoribonucleotides. In separate reactions, each oligonucleotide is mixed with an equivalent quantity (0.2 $A_{260}$ units) of its complementary oligonucleotide in 150 mM NaCl, 10 mM $Na_2PO_4$, 1 mM EDTA (pH 7.0). The mixture is heated to 85° C. for 5 minutes, then cooled to 30° C. The temperature is then increased from 30° C. to 80° C. at a rate of 1° C. per minute and $A_{260}$ is recorded as a function of temperature. Oligonucleotides according to the invention are expected to form duplexes with complementary oligodeoxyribonucleotides or oligoribonucleotides at temperatures well above physiological temperatures.

EXAMPLE 6

Inhibition of HIV-1 by Oligonucleotides Containing Primary Phosphoramidate Internucleoside Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 3, or by incorporating the protocol of Example 3 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266 (1992)). Oligonucleotides are tested for their abilty to inhibit HIV-1 in a tissue culture system. H9 lymphocytes are infected with HIV-1 virions (0.01–0.1 TCID$_{50}$/cell) for one hour at 37° C. After one hour, unadsorbed virions are washed away and the infected cells are divided among wells of 24 well plates. To the infected cells, an appropriate concentration (from stock solution) of oligonucleotide is added to obtain the required concentration (0.1–10 micromolar) in 2 ml media. The cells are then cultured for four days. At the end of four days, inhibition of HIV-1 is assessed by observing or measuring reductions in syncytium formation, p24 expression and reverse transcriptase activity. All of the tested oligonucleotides according to the invention are expected to show significant reductions in these parameters without significant cytotoxicity.

What is claimed is:

1. A mixed backbone oligonucleotide having from about 12 to about 50 nucleosides and containing primary phosphoramidate internucleoside linkages having the structure

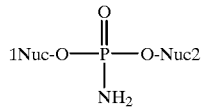

wherein "1Nuc" represents a 3' position of a first nucleoside and "Nuc2" represents a 5' position of a second nucleoside, and further comprising at least one nucleoside linkage that is not a primary phosphoramidate internucleoside linkage.

2. The mixed backbone oligonucleotide according to claim 1, wherein the internucleoside linkage(s) that are not primary phosphoramidate linkages are selected from the group consisting of phosphodiester and phosphorothioate internucleoside linkages.

3. A chimeric oligonucleotide comprising adjacent nucleosides comprising a first region of the oligonucleotide, which adjacent nucleosides are connected by primary phosphoramidate linkages, and other adjacent nucleosides comprising a second region of the oligonucleotide, which other adjacent nucleosides are connected by a different type of internucleoside linkage.

4. The chimeric oligonucleotide according to claim 3, wherein the second region is a phosphodiester or phosphorothioate region.

5. The chimeric oligonucleotide according to claim 4, wherein the phosphorothioate or phosphodiester region is flanked on either side by a primary phosphoramidate region.

6. The chimeric oligonucleotide according to claim 4, wherein the first region is flanked on either side by a phosphorothioate or phosphodiester region.

* * * * *